(12) United States Patent
Jensen et al.

(10) Patent No.: US 7,607,832 B2
(45) Date of Patent: Oct. 27, 2009

(54) APPARATUS FOR MEDICAL IMAGING

(75) Inventors: Vernon Thomas Jensen, Draper, UT (US); Samuel Lee Alder, Stansbury Park, UT (US); Gregory A Weaver, South Jordan, UT (US)

(73) Assignee: General Electric Company, Schenectady, NY (US)

( * ) Notice: Subject to any disclaimer, the term of this patent is extended or adjusted under 35 U.S.C. 154(b) by 38 days.

(21) Appl. No.: 11/563,020

(22) Filed: Nov. 23, 2006

(65) Prior Publication Data
US 2008/0123819 A1 May 29, 2008

(51) Int. Cl.
*H05G 1/02* (2006.01)
(52) U.S. Cl. .................... 378/197; 378/198
(58) Field of Classification Search .......... 378/197, 378/198
See application file for complete search history.

(56) References Cited
U.S. PATENT DOCUMENTS

| | | | | |
|---|---|---|---|---|
| 4,955,046 A | * | 9/1990 | Siczek et al. | 378/197 |
| 5,067,145 A | * | 11/1991 | Siczek et al. | 378/198 |
| 5,515,416 A | * | 5/1996 | Siczek et al. | 378/197 |
| 6,131,690 A | * | 10/2000 | Galando et al. | 180/411 |
| 6,431,751 B1 | * | 8/2002 | Everett et al. | 378/197 |
| 6,491,430 B1 | * | 12/2002 | Seissler | 378/207 |
| 6,609,826 B1 | * | 8/2003 | Fujii et al. | 378/198 |
| 7,188,998 B2 | * | 3/2007 | Gregerson et al. | 378/197 |
| 7,338,207 B2 | * | 3/2008 | Gregerson et al. | 378/198 |

* cited by examiner

*Primary Examiner*—Edward J Glick
*Assistant Examiner*—Thomas R Artman
(74) *Attorney, Agent, or Firm*—William Baxter; Michael G. Smith; Ellis B. Rairez

(57) ABSTRACT

Embodiments provide apparatus for medical imaging which includes: a base assembly including a set of wheels for rolling movement on a floor to transport the base assembly between locations; an imaging assembly for imaging the subject; and a movable support assembly connected between the base assembly and the imaging assembly for supporting the imaging assembly on the base assembly and for extending and retracting the imaging assembly from the base assembly. Embodiments provide apparatus for medical imaging wherein overall length of the apparatus with the imaging assembly extended exceeds overall length with the imaging assembly retracted.

20 Claims, 8 Drawing Sheets

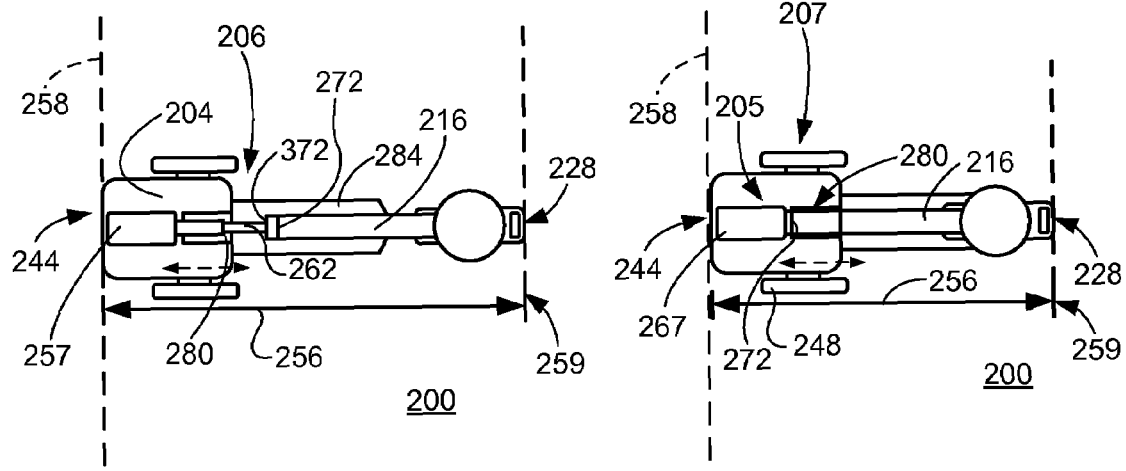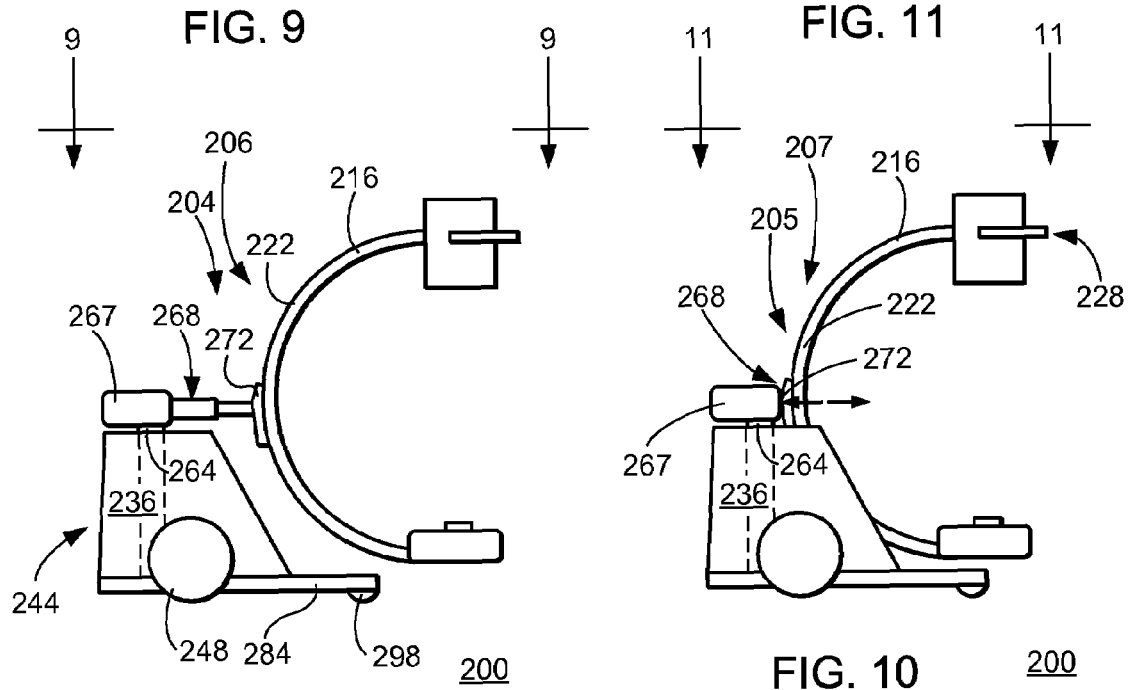

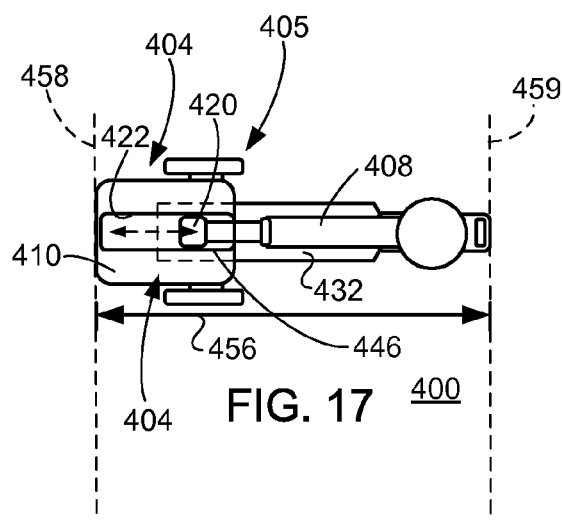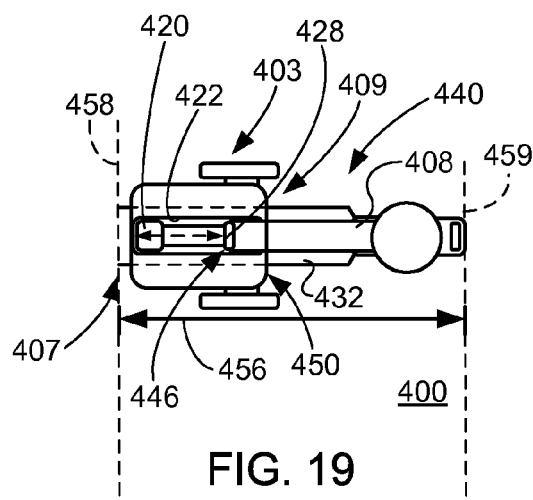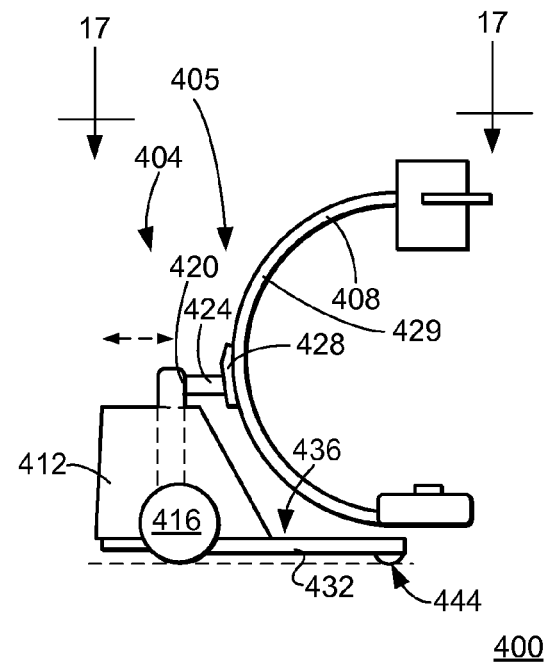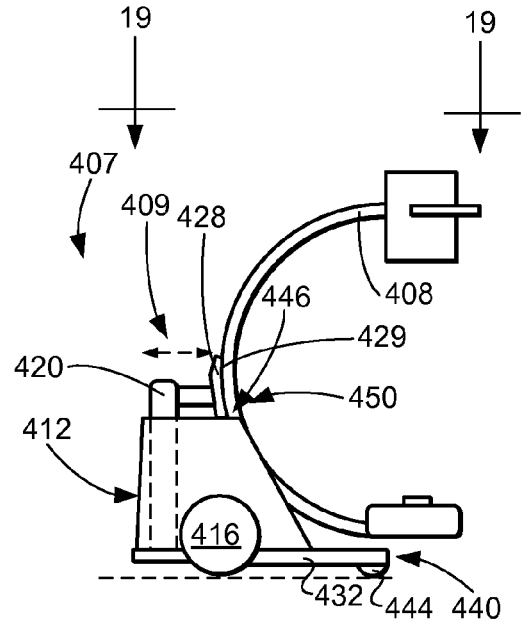
FIG. 17
FIG. 19
FIG. 16
FIG. 18

APPARATUS FOR MEDICAL IMAGING

FIELD OF THE INVENTION

The disclosure relates generally to apparatus for medical imaging.

BACKGROUND OF THE INVENTION

The present disclosure relates generally to apparatus for medical imaging. More particularly, embodiments of the present disclosure relate to mobile apparatus for medical imaging. As described herein, "mobile" is intended to describe apparatus for medical imaging which is movable between different locations in a medical facility. Embodiments of the present disclosure relate particularly to mobile apparatus for fluoroscopic medical imaging having a C-arm, O-arm, L-arm or other imaging assembly. Particularly, embodiments of the disclosure relate to mobile apparatus for medical imaging which includes a C-arm imaging assembly. Hereinafter such apparatus is referred to as a "mobile C-arm imaging system". As described herein, a mobile C-arm imaging system includes an imager suitable for generating an image of a subject, such as a human subject. In one common application, the imager includes an X-ray tube for generating X-rays to image the subject. A mobile C-arm imaging system includes a C-arm assembly which supports the imager, such as an X-ray tube, in a desired position relative to the subject to be imaged. A mobile C-arm imaging system also includes a base assembly which supports the C-arm assembly. The base assembly has a set of wheels for transporting the mobile C-arm imaging system between locations and for maneuvering the system into desired stationary positions at each location.

Mobile C-arm imaging systems are used in a variety of clinical environments, such as hospital radiology and surgery departments. As described above, the C-arm assembly typically supports an imager such as an X-ray tube in a desired position relative to the subject. In some configurations, the C-arm assembly remains stationary relative to the subject for single angle imaging. In other configurations, the C-arm assembly moves relative to the subject in order to acquire images from multiple angles. In some arrangements, the C-arm assembly is manually repositioned to generate images from different angles. In other arrangements, the C-arm assembly is moved along a predetermined path by operation of a motorized drive mechanism in order to generate images from multiple angles. Mobile C-arm imaging systems including motorized drive mechanisms for moving the C-arm assembly generally are larger and heavier than manual arrangements. Mobile C-arm imaging systems including larger, heavier, and more powerful X-ray tubes generally are larger and heavier than systems using smaller X-ray tubes.

Mobile C-arm imaging systems typically include a set of wheels for rolling the system across floors between different stationary imaging locations within a facility. Overall length and overall size of the system can limit the paths along which the system can be transported. For example, small passages such as elevators and confined corners can prevent systems from being rolled into various locations within a facility. Overall length and overall size can also limit locations which will accommodate the system in a stationary position for imaging. For example, use of a mobile C-arm imaging system in some operating rooms may be prevented or limited by overall length or overall size of the system. Also, operating rooms frequently are crowded with various equipment and personnel, and the overall length and size of a mobile C-arm imaging system can interfere with personnel and activities in the immediate vicinity of the operating table. The length of the C-arm assembly and the overall length of the system can limit the maneuverability of the system within a facility. Referring again to the operating room environment, and referring particularly to the crowded immediate vicinity around an operating table, maneuverability of the system relative to the operating table and the human subject can be limited by the length of the C-arm assembly and overall length of the system. Mobile C-arm imaging systems can pose a tipping hazard, in part because the length and mass of the C-arm assembly negatively influences the center of gravity. Typically, the hazard of tipping is increased when a mobile C-arm imaging system is rolled across an incline during transport. Lateral swinging of the C-arm assembly can damage the C-arm assembly, personnel or material impacted by the C-arm assembly.

The C-arm assembly can support several hundred kilograms of mass in an elevated position, and the C-arm assembly can be repositioned or rotated between imaging scans. A mobile C-arm imaging system includes a body which serves as a counterweight to the elevated mass of the C-arm. Adding a unit of mass to the distal end of the C-arm assembly requires an increase of several units of mass in the overall weight of the system. Such a weight increase is necessary in order to increase the mass of the base assembly and counterbalance the increased, elevated mass of the C-arm assembly. Mobile C-arm imaging systems having heavier C-arms and base assembly bodies generally are larger and consequently require more space than lighter systems. Increased system mass and size reduce positioning flexibility around the surgical table, reduce maneuverability for transporting the mobile C-arm system between imaging locations within a facility, increase the amount of material necessary to manufacture each system, and increase the cost of shipping systems.

BRIEF DESCRIPTION OF THE INVENTION

Embodiments of the present disclosure provide improved apparatus for medical imaging. The above-mentioned shortcomings, disadvantages and problems are addressed herein. For reasons stated above, and for other reasons stated below which will become apparent to those skilled in the art upon reading and understanding the present specification, there is a need in the art for improved mobile apparatus for medical imaging.

In one aspect, an embodiment provides an apparatus for imaging a subject, the apparatus including: a base assembly including a set of wheels for rolling movement on a floor, an imaging assembly for imaging the subject, and a movable support assembly connected between the base assembly and the imaging assembly for supporting the imaging assembly on the base assembly and for extending and retracting the imaging assembly from the base assembly.

In one aspect, an embodiment provides an apparatus for imaging a subject, the apparatus including: an imaging assembly for imaging the subject, a base assembly having a front end portion adjacent the imaging assembly, and a movable support assembly connected between the base assembly and the imaging assembly for supporting the imaging assembly on the base assembly and for extending and retracting the imaging assembly on the base assembly. The movable support assembly in a transport condition supports the imaging assembly in a retracted position, and in a stationary imaging condition supports the imaging assembly in an extended position. The apparatus has an overall length with the imaging assembly in the extended position exceeding the overall length with the imaging assembly in the retracted position.

In one aspect, an embodiment provides an apparatus for imaging a subject, the apparatus including: an imaging assembly, a base assembly, and a movable support assembly. The movable support assembly supports the imaging assembly and is selectively operable to move the imaging assembly relative to the body between an extended position and a retracted position. In the retracted position no portion of the base assembly extends in the rear direction beyond the vertical rear plane. In the extended position the apparatus has an overall length exceeding the overall length with the imaging assembly in the retracted position.

Apparatus embodiments of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 8 is a simplified side elevation view of apparatus for medical imaging in a stationary imaging condition according to an embodiment.

FIG. 9 is a top view of apparatus for medical imaging in the stationary imaging condition and taken generally along line 9-9 in FIG. 8.

FIG. 10 is a simplified side elevation view of apparatus for medical imaging in a transport condition.

FIG. 11 is a top view of apparatus for medical imaging in the transport condition and taken generally along line 11-11 in FIG. 10.

FIG. 16 is a simplified side elevation view of apparatus for medical imaging in a stationary imaging condition according to an embodiment.

FIG. 17 is a top view of apparatus for medical imaging in the stationary imaging condition and taken generally along line 17-17 in FIG. 16.

FIG. 18 is a simplified side elevation view of apparatus for medical imaging in a transport condition.

FIG. 19 is a top view of apparatus for medical imaging in the transport condition and taken generally along line 19-19 in FIG. 18.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
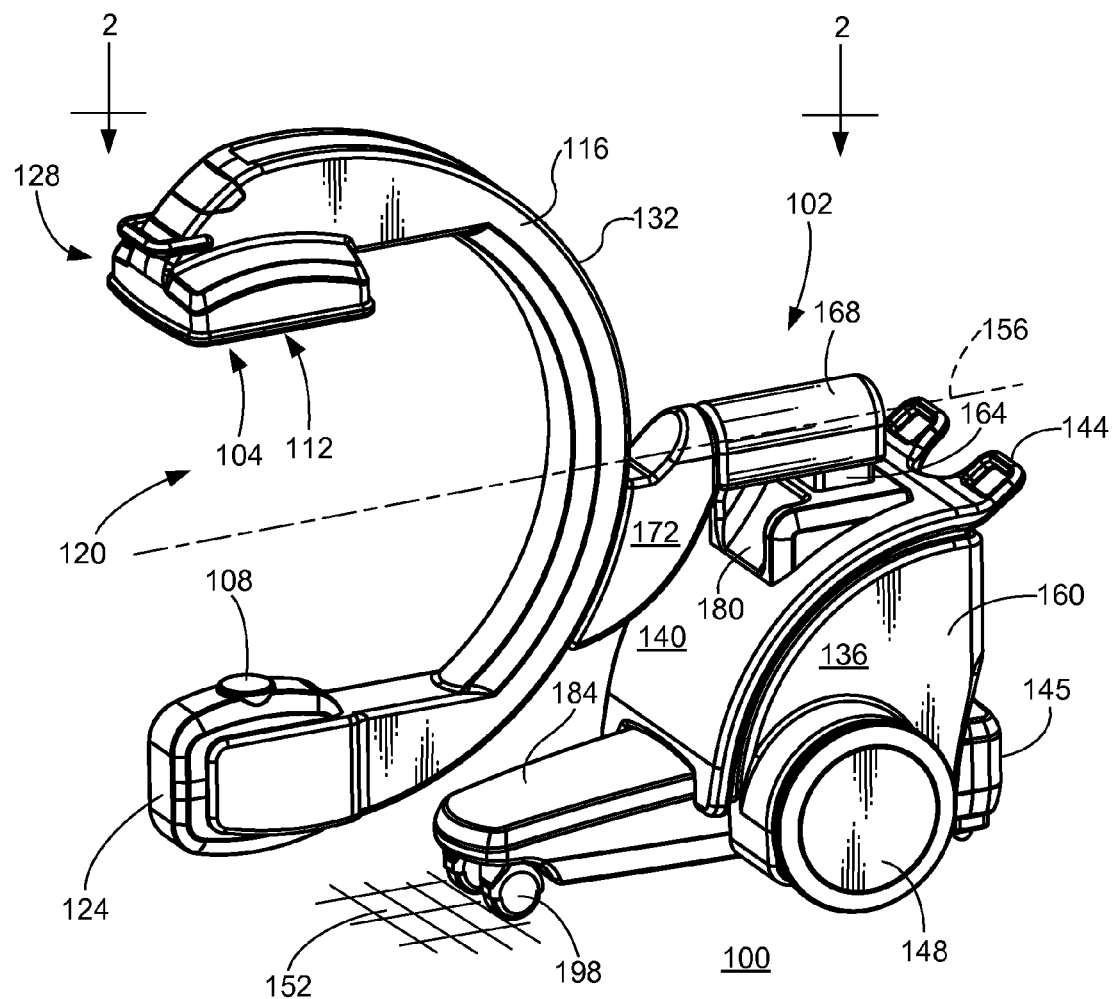
FIG. 1 is a front perspective view of apparatus for medical imaging in a stationary imaging condition according to an embodiment.

FIG. 1 is a front perspective view of apparatus 100 for medical imaging in a stationary imaging condition according to an embodiment. Apparatus 100 includes an imager 104. Imager 104 is operable to generate medical images of a subject (not shown), such as a human subject. Imager 104 can include any suitable imaging apparatus. In the illustrated embodiment, imager 104 includes an X-ray tube 108 operable to generate X-rays for imaging the subject. In the illustrated embodiment, imager 104 includes a detection apparatus 112 operable to generate a medical image of the subject. It is to be understood that different imagers can be used. Further, it is to be understood that the apparatus 100 can include different arrangements of the imager 104. For example, some components may be present or omitted in different arrangements of the imager 104.

Apparatus 100 includes an imaging assembly 116 supporting the imager 104. In the illustrated embodiment, the imaging assembly 116 is a C-arm imaging assembly supporting the imager 104. It is to be understood that the present disclosure is not limited to systems including a C-arm imaging assembly and, in other embodiments (not shown), imaging assembly 116 can be of different construction. In other embodiments of the present disclosure, for example, imaging assembly 116 can be an O-arm or L-arm imaging assembly. Referring again to the illustrated embodiment, imaging assembly 116 has a front opening 120 to accommodate the subject being imaged. Imaging assembly 116 includes lower distal end 124. Lower distal end 124 supports X-ray tube 108. Imaging assembly 116 includes upper distal end 128. Upper distal end 128 is spaced from lower distal end 124 in the vertical direction. Upper distal end 128 supports detection apparatus 112. Spaced lower distal end 124 and upper distal end 128 cooperate to define front opening 120. Imaging assembly 116 includes curved back segment 132. Back segment 132 extends between and supports spaced lower distal end 124 and upper distal end 128. Back segment 132 is oriented in general opposition to front opening 120. Back segment 132 is spaced from front opening 120 in the rearward direction along longitudinal axis 156. Front opening 120 is spaced from back segment 132 in the forward direction along longitudinal axis 156. Back segment 132 includes capture unit 172. Capture unit 172 is connected to and supported by movable support assembly 161 in rotatable relation thereto by a rotation knuckle (not shown) mounted on a cross arm 168.

Returning to FIG. 1, apparatus 100 includes base assembly 160. Base assembly 160 supports imaging assembly 116 for selective motion and positioning relative thereto, as further described below. Base assembly 160 includes body 136. Body 136 includes front end portion 140 adjacent the imaging assembly 116. More particularly, front end portion 140 is adjacent back segment 132 of the imaging assembly 116. Particularly, front end portion 140 is adjacent a portion of capture unit 172 of back segment 132. Front end portion 140 has therein a recessed dock 180. Recessed dock 180 defines a recess or space and is adapted to receive therein a portion of back segment 132. More particularly, recessed dock 180 is adapted to receive a portion of capture unit 172 of back segment 132. Recessed dock 180 is defined between a pair of spaced, opposing sidewalls confining lateral motion of capture unit 172, back segment 132 and imaging assembly 116 relative to front end portion 140 of body 136. Recessed dock 180 includes a recessed rest extending between the spaced sidewalls. The recessed rest of recessed dock 180 confines longitudinal motion and vertical motion of capture unit 172, back segment 132 and imaging assembly 116 relative to front end portion 140 of body 136.

Figure 2:
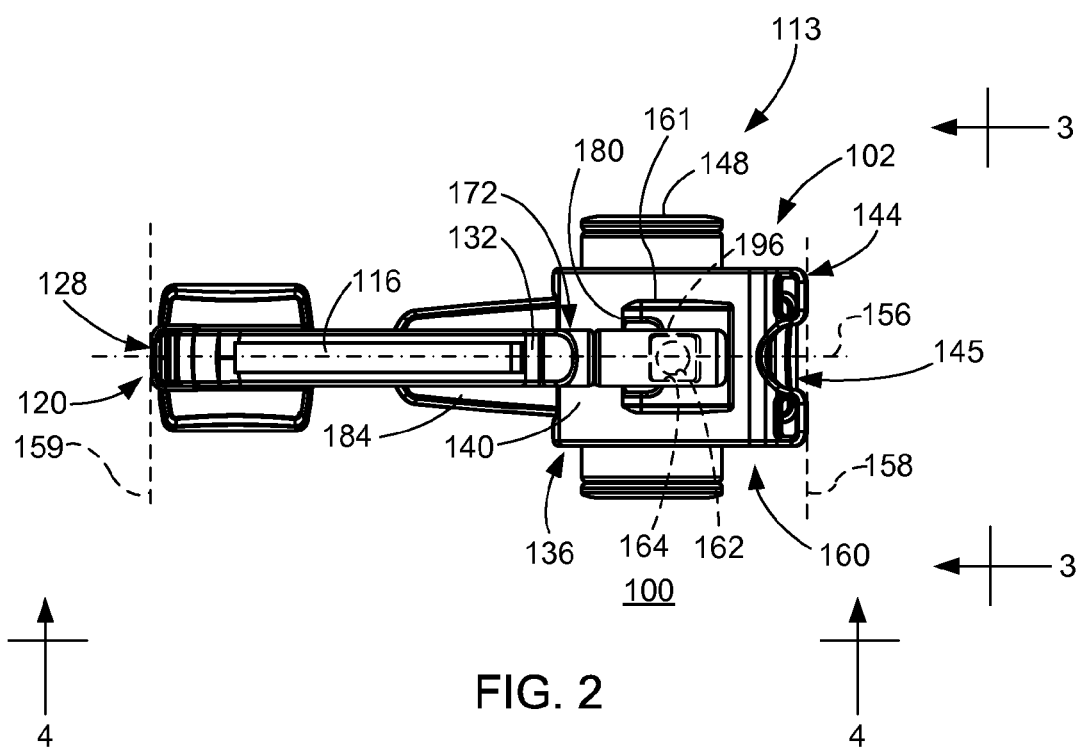
FIG. 2 is a top view of apparatus for medical imaging in the stationary imaging condition and taken generally along line 2-2 in FIG. 1.

Body 136 includes rear end 144. Rear end 144 is spaced from front end portion 140 in the rearward direction along longitudinal axis 156. Referring to FIG. 2, rear vertical plane 158 is defined by and intersects rear end 144. Rear vertical plane 158 is perpendicular to longitudinal axis 156. In the illustrated embodiment, rear end 144 is defined by a pair of grip handles adapted for gripping by personnel to transport and maneuver base assembly 160.

Base assembly 160 includes a set of wheels 148 for rolling movement on the floor 152. The set of wheels 148 supports body 136 in a transport condition for rolling movement between stationary imaging locations in a facility. The set of wheels 148 supports body 136 in a stationary imaging condition at each stationary imaging location. In the illustrated embodiment, the set of wheels 148 includes a pair of spaced primary wheels of large diameter.

Referring to FIG. 1, base assembly 160 includes stabilizing foot 184 adapted for engagement with the facility floor 152. Stabilizing foot 184 extends in the forward direction from the front end portion 140. Stabilizing foot 184 has a rear end 145. Stabilizing foot includes a set of stabilizing wheels 198 which engage the facility floor for rolling movement relative thereto. In the illustrated embodiment, stabilizing wheels 198 includes a pair of closely spaced forward stabilizing wheels in the forward direction of the front end portion 140 and stabilizing foot 184. In the illustrated embodiment, stabilizing wheels 198 includes a set of closely spaced rear stabilizing wheels (see FIG. 3). Stabilizing wheels 198 are of smaller diameter than primary wheels 148 and are mounted for pivotal motion relative to a respective vertical axis for performing tight radius turns.

Referring to FIG. 1, apparatus 100 includes movable support assembly 161 supporting imaging assembly 116. Movable support assembly 161 is coupled between the base assembly 160 and the imaging assembly 116 for supporting the imaging assembly 116 on the base assembly 160 and for extending and retracting the imaging assembly 116 from the base assembly 160. In an embodiment, movable support assembly 161 includes a lift column 162 (see FIG. 2) having a bearing block 164 (see FIG. 1). Referring to FIG. 2, lift column 162 is supported by body 136 and extends generally in the vertical direction relative thereto. Lift column 162 is an elongated tubular member mounted on body 136. It is to be understood that lift column 162 can be of any suitable construction. Lift column 162 extends in the vertical direction relative to body 136. Lift column 162 includes a bearing block 164 mounted on the upper end thereof. Movable support assembly 161 includes cross arm 168 mounted on the bearing block 164 of the lift column 162. Cross arm 168 extends in the horizontal direction relative to the bearing block 164 of lift column 162. In the embodiment illustrated in FIG. 1, cross arm 168 is movable along the longitudinal axis 156 in the forward and rearward directions relative to the bearing block 164 of lift column 162. More particularly, cross arm 168 is movable in the forward direction to a front position 102 relative to bearing block 164 of lift column 162. Cross arm 168 is movable in the rearward direction to a rear position 103 (see FIG. 5) relative to bearing block 164 of lift column 162. More particularly, cross arm 168 is movable in the rearward direction to rear position 103 relative to bearing block 164 of lift column 162 without extending in the rearward direction beyond vertical rear plane 158. It is to be understood that cross arm 168 can be of any suitable construction which is movable in the forward direction to a front position 102 relative to bearing block 164 of lift column 162 and is movable in the rearward direction to rear position 103 relative to bearing block 164 of lift column 162 without extending in the rearward direction beyond vertical rear plane 158. In the illustrated embodiment, cross arm 168 includes a telescoping arrangement of stacked members (not shown) which are movable by telescoping motion relative to the bearing block 164 of lift column 162. In the specific arrangement illustrated, the telescoping arrangement of stacked members includes a hydraulically operable telescoping arrangement of an inner tubular member stacked within an outer tubular member. In other embodiments (not shown), cross arm 168 can include any other suitable construction or arrangement which enables movement along the longitudinal axis 156 in the forward and rearward directions relative to the bearing block 164 of lift column 162 without extending in the rearward direction beyond vertical rear plane 158. Examples of suitable constructions of cross arm 168 include: a hinged arrangement of members, a folding arrangement of members, a trained arrangement of linked members, a member which is movable along a curved or nonlinear path, a member which is movable along a non-horizontal path, a pivotable arrangement of members joined by elbow linkages, a rack and pinion arrangement, and an arrangement of hydraulic components. Movable support assembly 161 includes a rotation knuckle (not shown) mounted on a forward end of cross arm 168. The rotation knuckle is connected to capture unit 172 of back segment 132 of imaging assembly 116 and thus supports imaging assembly 116 on the cross arm 168. The rotation knuckle can be manipulated to rotate and position imaging assembly 116 to a desired angular orientation for imaging.

FIG. 2 is a top view of apparatus 100 for medical imaging in the stationary imaging condition and taken generally along 2-2 in FIG. 1. Cross arm 168 is moved to the front position 113 relative to the bearing block 164 of lift column 162. Cross arm 168 being in the front position brings the imaging assembly 116 into the extended position 102. Overall length of apparatus 100 for medical imaging in the stationary imaging condition is measured along the longitudinal axis 156 between vertical forward plane 159 and vertical rear plane 158.

Figure 3:
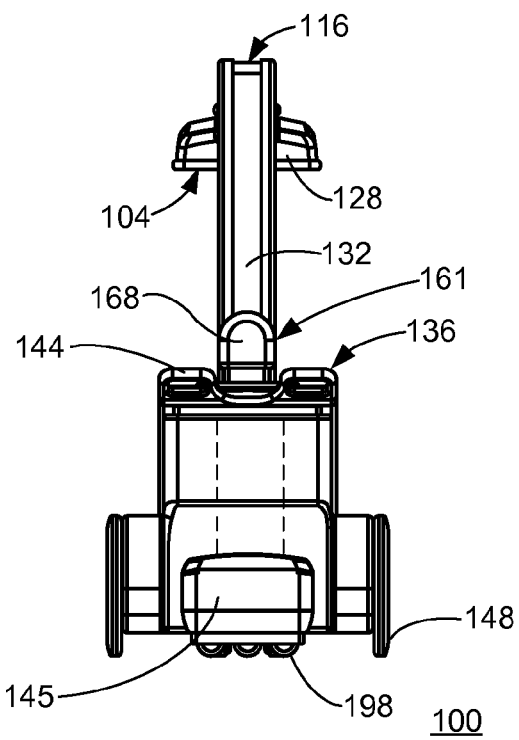
FIG. 3 is a rear elevation view of apparatus for medical imaging in the stationary imaging condition and taken generally along line 3-3 in FIG. 2.

FIG. 3 is a rear elevation view of apparatus 100 for medical imaging in the stationary imaging condition and taken generally along line 3-3 in FIG. 2. Rear end 145 of stabilizing foot 184 (not shown in FIG. 3) is shown. Movable support assembly 161 including cross arm 168 and bearing block 164 of lift column 162 are shown. Rear end 144 is also shown.

Figure 4:
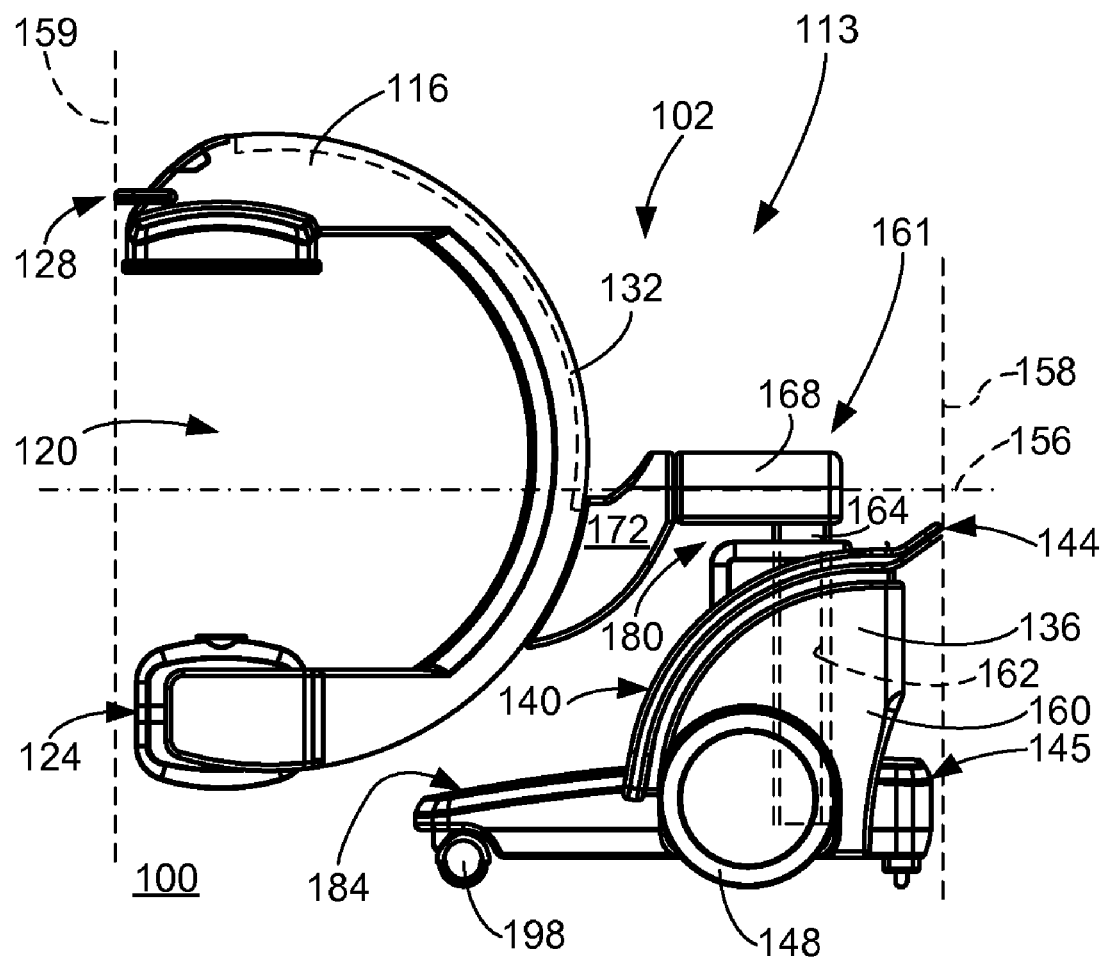
FIG. 4 is a side elevation view of apparatus for medical imaging in the stationary imaging condition and taken generally along line 4-4 in FIG. 2.

FIG. 4 is a side elevation view of apparatus 100 for medical imaging in the stationary imaging condition and taken generally along line 4-4 in FIG. 2. Vertical rear plane 158 extends through rear end 144. No other portion of apparatus 100 extends in the rearward direction beyond vertical rear plane 158. Overall length of apparatus 100 is measured along longitudinal axis 156 between vertical front plane 159 and vertical rear plane 158. Elongated vertical lift column 162 including bearing block 146 is shown. Cross arm 168 is moved to the front position 113 relative to bearing block 164 of lift column 162 and brings imaging assembly 116 into the extended position 102 relative to base assembly 160. In extended position 102, capture unit 172 of back segment 132 of imaging assembly 116 is adjacent and spaced in the forward direction from front end portion 140 of body 136.

Figure 5:
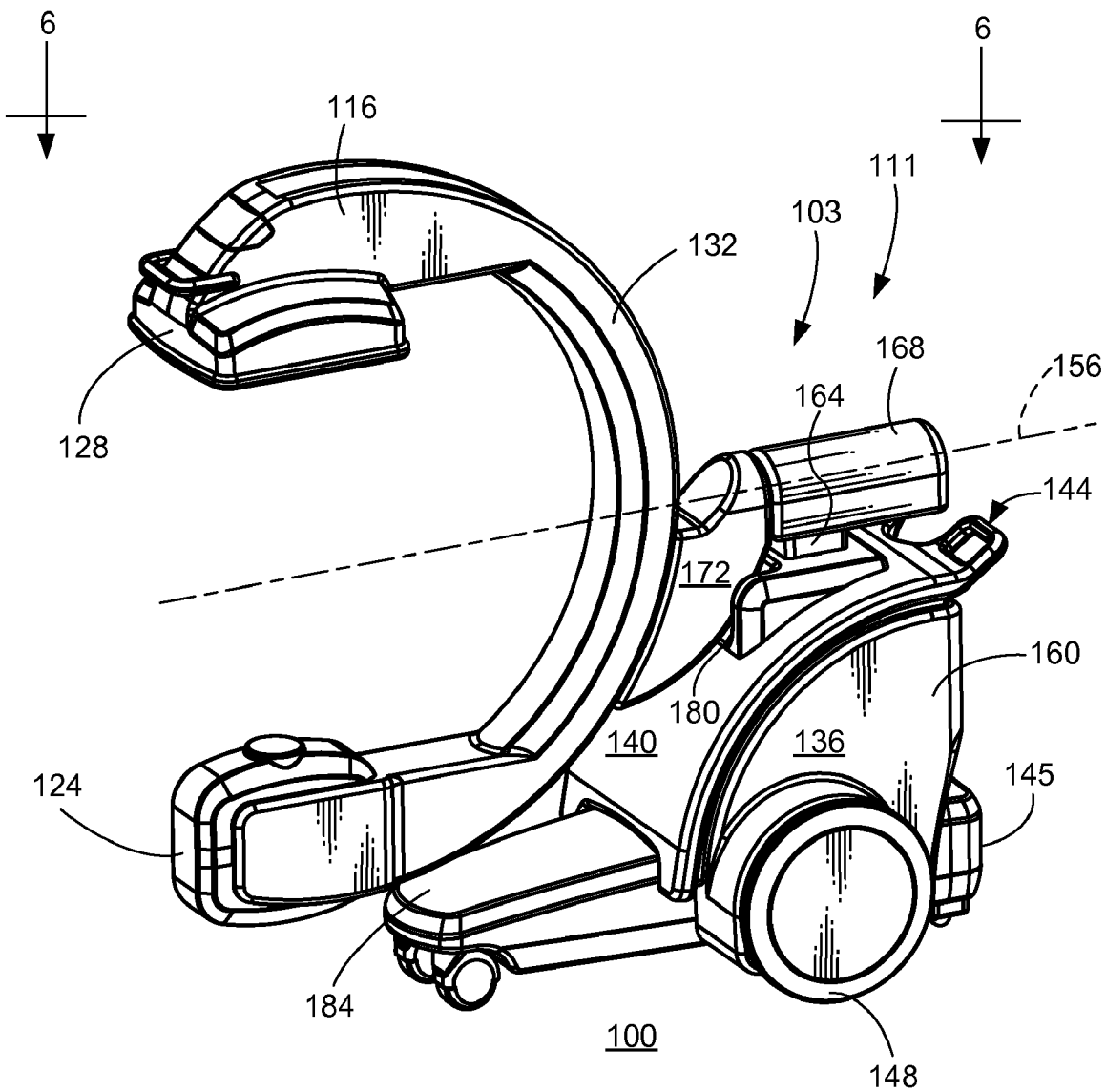
FIG. 5 is a front perspective view of apparatus for medical imaging in a transport condition.

FIG. 5 is a front perspective view of apparatus 100 for medical imaging in a transport condition. Cross arm 168 is moved in the rearward direction along the longitudinal axis 156 to a rear position 111 relative to the bearing block 164 of lift column 162. Cross arm 168 being in the rear position 111 brings imaging assembly 116 into a retracted position 103 relative to base assembly 160. In retracted position 103, a portion of capture unit 172 of back segment 132 of imaging assembly 116 is adjacent front end portion 140 of body 136. In retracted position 103, a portion of capture unit 172 of back segment 132 of imaging assembly 116 is received in recessed dock 180 between the sidewalls.

Figure 6:
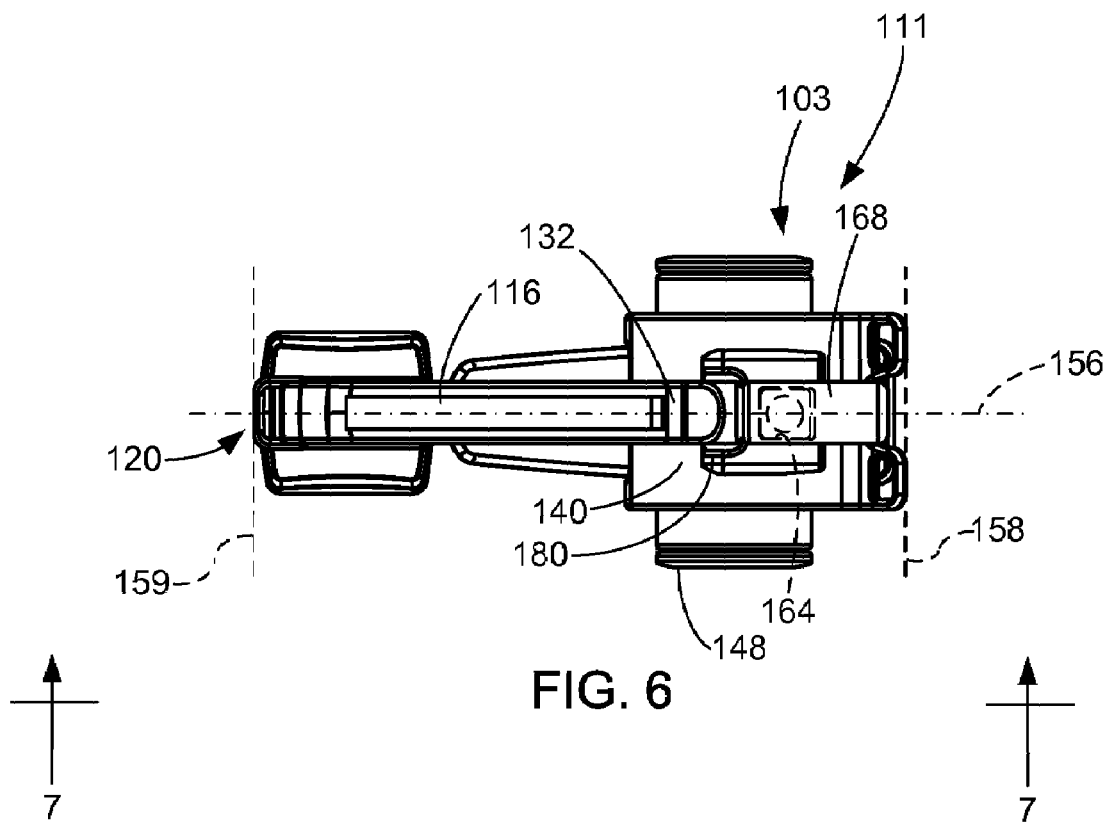
FIG. 6 is a top view of apparatus for medical imaging in the transport condition and taken generally along line 6-6 in FIG. 5.

FIG. 6 is a top view of apparatus 100 for medical imaging in the transport condition and taken generally along 6-6 in FIG. 5. With cross arm 168 in the rear position 111 bringing imaging assembly into retracted position 103, no portion of cross arm 168, movable support assembly 161 or base assembly 160 extends in the rearward direction along longitudinal axis 156 beyond vertical rear plane 158. Overall length of apparatus 100 for medical imaging in the transport condition is measured along longitudinal axis 156 between vertical forward plane 159 and vertical rear plane 158 with cross arm 168 in the rear position 111 bringing imaging assembly into retracted position 103. Overall length of apparatus 100 for medical imaging in the transport condition (shown in FIG. 6) with cross arm 168 in the rear position 111 bringing imaging assembly 116 into retracted position 103 is less than overall length of apparatus 100 for medical imaging in the stationary imaging condition (shown in FIG. 2) with cross arm 168 in the front position 113 bringing imaging assembly 116 into extended position 102.

Figure 7:
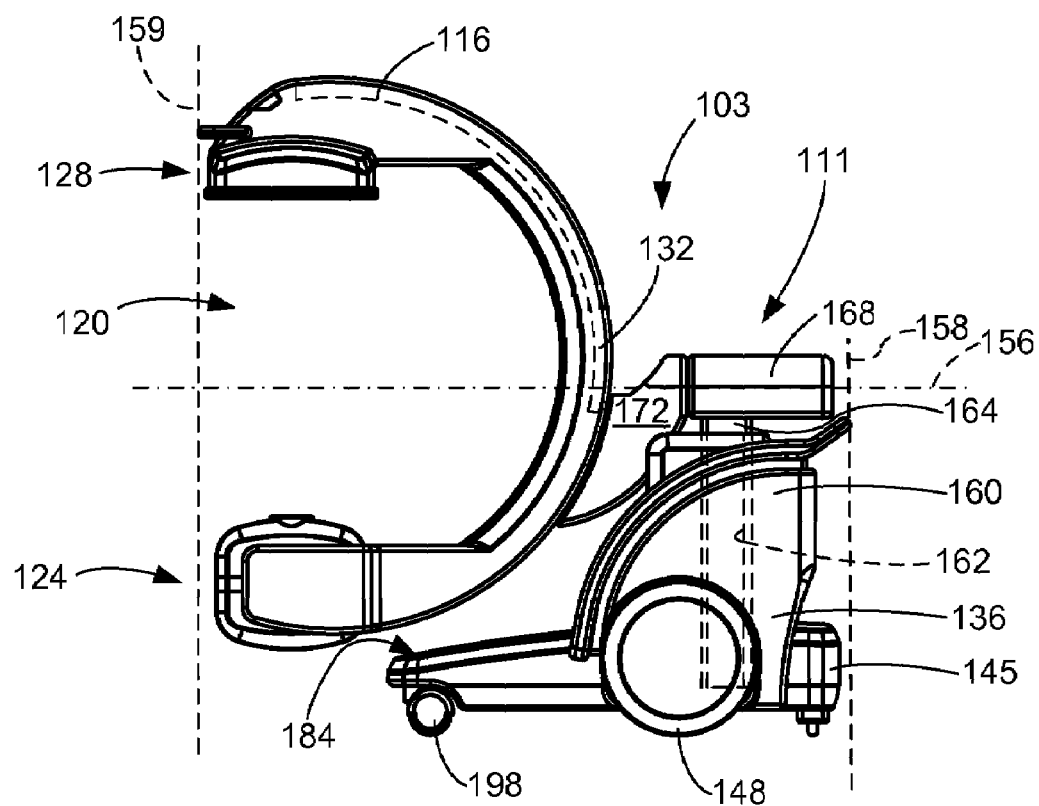
FIG. 7 is a side elevation view of apparatus for medical imaging in the transport condition and taken generally along line 7-7 in FIG. 6.

FIG. 7 is a side elevation view of apparatus 100 for medical imaging in the transport condition and taken generally along 7-7 in FIG. 6. With cross arm 168 in the rear position 111 relative to bearing block 164 of vertical lift column 162 bringing imaging assembly into retracted position 103, no portion of cross arm 168, movable support assembly 161 or base assembly 160 extends in the rearward direction along longitudinal axis 156 beyond vertical rear plane 158. In retracted position 103, a portion of capture unit 172 of back segment 132 of imaging assembly 116 is adjacent front end portion 140. In retracted position 103, a portion of capture unit 172 of back segment 132 of imaging assembly 116 is received in recessed dock 180.

FIG. 8 is a simplified side elevation view of apparatus 200 for medical imaging in a stationary imaging condition according to an embodiment. Base assembly 236 is supported by wheels 248, 298 for rolling movement across the facility floor. Base assembly 236 includes stabilizing foot 284 supported by wheels 298 and extending in the forward direction. Cross arm 267 includes a hydraulically operable telescoping arrangement 268 of stacked tubular members. Telescoping arrangement 268 of cross arm 267 is moved in the forward direction to a front position 204 relative to bearing block 264 of the vertical lift column 262. Telescoping arrangement 268 of cross arm 267 being moved to the front position 204 brings the imaging assembly 216 into an extended position 206 relative to base assembly 236 for imaging a subject. Telescoping arrangement 268 of stacked tubular members of cross arm 267 supports capture unit 272 of back segment 222 of imaging assembly 216 in the extended position 206.

FIG. 9 is a top view of apparatus 200 for medical imaging in the stationary imaging condition taken generally along 9-9 in FIG. 8. Overall length of apparatus 200 for medical imaging in the stationary imaging condition with cross arm 267 moved to the front position 204 bringing imaging assembly 216 into the extended position 206 is measured along longitudinal axis 256 between vertical forward plane 259 and vertical rear plane 258.

FIG. 10 is a simplified side elevation view of apparatus 200 for medical imaging in a transport condition. Telescoping arrangement 268 of cross arm 267 is moved in the rearward direction to a rear position 205 relative to bearing block 264 of the vertical lift column 262. Telescoping arrangement 268 of cross arm 267 being moved to the rear position 205 brings the imaging assembly 216 into a retracted position 207 relative to base assembly 236 for transport between locations in a facility. A portion of capture unit 272 and a further portion of back segment 222 are received in recessed dock 280 in front end portion 240 of body 260.

FIG. 11 is a top view of apparatus 200 for medical imaging in a transport condition and taken generally along 11-11 in FIG. 10. Overall length of apparatus 200 for medical imaging in the transport condition is measured along longitudinal axis 256 between vertical forward plane 259 and vertical rear plane 258. Overall length of apparatus 200 for medical imaging in the transport condition (shown in FIG. 11) with cross arm 267 in the rear position 205 bringing imaging assembly 216 into the retracted position 207 is less than overall length of apparatus 200 for medical imaging in the stationary imaging condition (shown in FIG. 9) with cross arm 267 in the front position 204 bringing imaging assembly 216 into the extended position 206.

Figure 12:
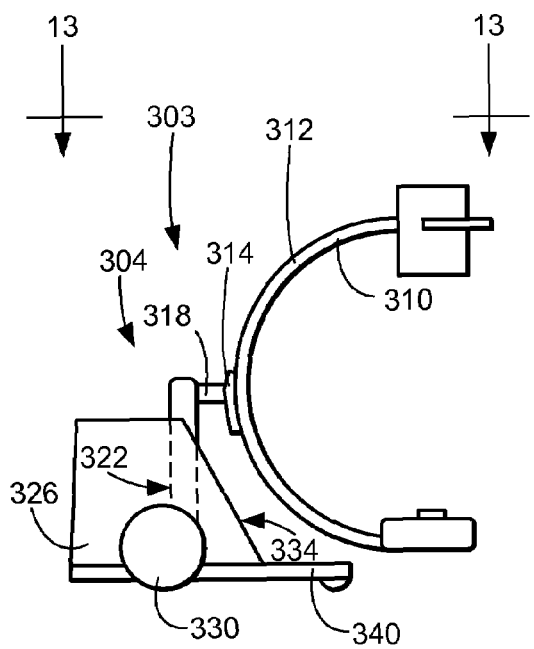
FIG. 12 is a simplified side elevation view of apparatus for medical imaging in a stationary imaging condition according to an embodiment.

FIG. 12 is a simplified side elevation view of apparatus 300 for medical imaging in a stationary imaging condition according to an embodiment. In the stationary imaging condition, vertical lift column 322 is moved to a front position 304 relative to body 326. Horizontal cross arm 318 is supported by lift column 322 in fixed relation thereto. It is to be understood that cross arm 318 can be supported in movable relation to lift column 318 as previously described herein. Cross arm 318 supports capture unit 314 of back segment 312 of imaging assembly 310. Lift column 322 being moved to the front position 304 brings the imaging assembly 310 into an extended position 303 relative to body 326 for imaging the subject. Lift column 322 is movable in relative to body 326 between front position 304 and rear position 305 (shown in FIG. 14).

Figure 13:
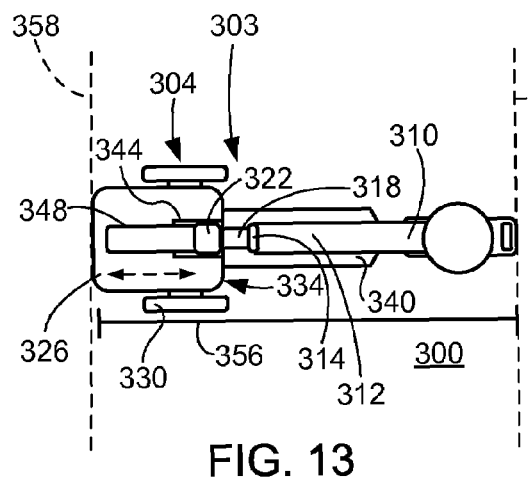
FIG. 13 is a top view of apparatus for medical imaging in the stationary imaging condition and taken generally along line 13-13 in FIG. 12.

FIG. 13 is a top view of apparatus 300 for medical imaging in the stationary imaging condition and taken generally along 13-13 in FIG. 12. Overall length of apparatus 300 for medical imaging in the stationary imaging condition is measured along longitudinal axis 356 between vertical forward plane 359 and vertical rear plane 358. Front recess 344 does not receive capture unit 314 of back segment 312 of imaging assembly 310 when imaging assembly is in the extended position 303. Lift column 322 is moved to the front position 304 of body 326 in body valley 348.

Figure 14:
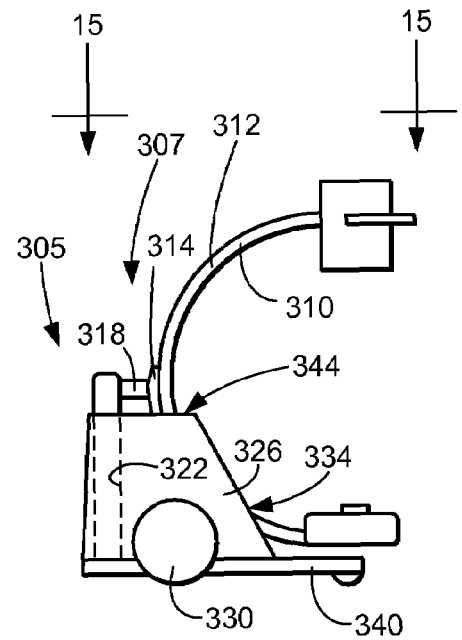
FIG. 14 is a simplified side elevation view of apparatus for medical imaging in a transport condition.

FIG. 14 is a simplified side elevation view of apparatus 300 for medical imaging in a transport condition. Lift column 322 is moved in the rearward direction relative to body 326 in body valley 348 to a rear position 305. Lift column 322 being moved to the rear position 305 brings the imaging assembly 310 into a retracted position 307 relative to body 326 for transport between locations in a facility. A portion of capture unit 314 and a further portion of back segment 312 of imaging assembly 310 are received in recessed dock 344 in front end portion 334 of body 326.

Figure 15:
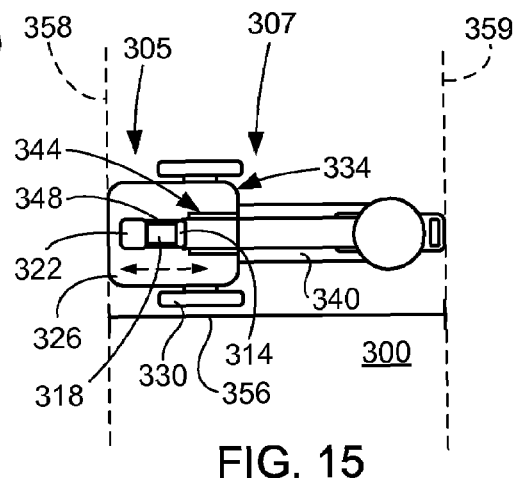
FIG. 15 is a top view of apparatus for medical imaging in the transport condition and taken generally along line 15-15 in FIG. 14.

FIG. 15 is a top view of apparatus 300 for medical imaging in the transport condition and taken generally along 15-15 in FIG. 14. Lift column 322 is moved in the rearward direction relative to body 326 in body valley 348 to a rear position 305. Lift column 322 being moved to the rear position 305 brings the imaging assembly 310 into a retracted position 307 relative to body 326 for transport between locations in a facility. A portion of capture unit 314 and a further portion of back segment 312 of imaging assembly 310 are received in recessed dock 344 in front end portion 334 of body 326. Overall length of apparatus 300 for medical imaging in the transport condition is measured along longitudinal axis 356 between vertical forward plane 359 and vertical rear plane 358. Overall length of apparatus 300 for medical imaging in the transport condition (shown in FIG. 15) with lift column 322 in the rear position 305 bringing imaging assembly 310 into the retracted position 307 is less than overall length of apparatus 300 for medical imaging in the stationary imaging condition (shown in FIG. 13) with lift column 322 in the front position 304 bringing imaging assembly 310 into the extended position 303.

FIG. 16 is a simplified side elevation view of apparatus 400 for medical imaging in a stationary imaging condition according to an embodiment. Apparatus 400 for medical imaging is similar to previously described apparatus 300 for medical imaging in that the lift column 420 is movable relative to body 412 in a body valley 422 between a rear position 407 (FIG. 16 and FIG. 17) bringing imaging assembly 408 into the retracted position 409 in the transport condition and a front position 404 (FIG. 18 and FIG. 19) bringing imaging assembly 408 into the extended position 405 in the stationary imaging condition. In the stationary imaging condition, vertical lift column 420 is moved to the front position 404 relative to body 412. Horizontal cross arm 424 is supported by lift column 420 in fixed relation thereto. It is to be understood that cross arm 424 can be supported in movable relation to lift column 420 as previously described herein. Cross arm 424 supports capture unit 428 of back segment 429 of imaging assembly 408. Lift column 420 being moved to the front position 404 brings the imaging assembly 408 into the extended position 405 relative to body 412 in the stationary imaging condition. Lift column 420 is movable in relation to body 412 between front position 404 and the rear position 407 (shown in FIG. 18).

Base assembly 410 includes stabilizing foot 432. Stabilizing foot 432 is movable relative to body 412 in the forward and rearward directions along the longitudinal axis 456 (see FIG. 17). Returning to FIG. 16, stabilizing foot 432 includes a set of stabilizing wheels 444 which engage the facility floor for rolling movement relative thereto. Stabilizing foot 432 is movable relative to body 412 between a stationary support position (FIG. 16 and FIG. 17) and a transport position (FIG. 18 and FIG. 19). Stabilizing foot 432 in the transport position (FIG. 18) is retracted in the rearward direction relative to body 412. Stabilizing foot 432 in the stationary support position (FIG. 16) is extended in the forward direction relative to body 412.

FIG. 17 is a top view of apparatus 400 for medical imaging in the stationary imaging condition and taken generally along 17-17 in FIG. 16. Overall length of apparatus 400 for medical imaging in the stationary imaging condition is measured along longitudinal axis 456 between vertical forward plane 459 and vertical rear plane 458. In the stationary imaging condition, cross arm 420 in the front position 404 brings imaging assembly 408 into the extended position 405, and stabilizing foot 432 in the stationary support position (FIG. 16) is extended in the forward direction relative to body 412.

FIG. 18 is a simplified side elevation view of apparatus 400 for medical imaging in a transport condition. Lift column 420 is moved in the rearward direction relative to body 412 to a rear position 407. Lift column 420 being moved to the rear position 407 brings the imaging assembly 406 into the retracted position 409 relative to body 412 for transport between locations in a facility. Stabilizing foot 432 in the transport position is retracted in relation to body 412. A portion of capture unit 428 and a further portion of back segment 429 of imaging assembly 408 are received in recessed dock 446 (see FIG. 19) in front end portion 450 of body 412.

FIG. 19 is a top view of apparatus 400 for medical imaging in a transport condition and taken generally along 19-19 in FIG. 18. Overall length of apparatus 400 for medical imaging in the transport condition is measured along longitudinal axis 456 between vertical forward plane 459 and vertical rear plane 458. Overall length of apparatus 400 for medical imaging in the transport condition (shown in FIG. 19) with lift column 420 in the rear position 407 bringing imaging assembly 408 into the retracted position 409 is less than overall length of apparatus 400 for medical imaging in the stationary imaging condition (shown in FIG. 17) with lift column 420 in the front position 404 bringing imaging assembly 408 into the extended position 405.

Embodiments provide a mobile imaging system including a set of wheels for rolling across floors between different stationary imaging locations within a facility and having an overall length in the transport condition with the imaging assembly in a retracted position that is less than the overall length in the stationary imaging condition with the imaging assembly in the extended position. Embodiments provide a mobile imaging system including a set of wheels for rolling across floors between different stationary imaging locations and in the transport condition with the imaging assembly in a retracted position no portion of the apparatus extends in the rearward direction beyond the vertical rear plane. Embodiments thus provide a mobile imaging system which can be transported along paths including small passages, such as in smaller elevators and around more confined corners, that otherwise prevent longer systems from being transported therein. Embodiments provide a mobile imaging system having an overall length and overall size which can be accommodated in a smaller, more confined space. Embodiments provide a mobile imaging system of reduced overall length and overall size which can be more readily accommodated in some operating room environments, and which has reduced spatial interference with personnel and activities in the immediate vicinity of the operating table. Embodiments provide a mobile imaging system having improved maneuverability, particularly because overall length of the system in the transport condition with the imaging assembly in the retracted position is less than the overall length of the system in the stationary imaging condition with the imaging assembly in the extended position. Embodiments provide a mobile imaging system which has a reduced likelihood of tipping and a reduced likelihood of tipping when rolled across an incline in the transport condition, because overall length is reduced and because a portion of the imaging assembly is received in the recessed dock in the front end portion of the body in the transport condition. Embodiments provide a mobile imaging system wherein lateral swinging of the imaging assembly relative to the base assembly is reduced by a portion of the back segment of the imaging assembly being received in the recessed dock in the front end portion of the body. Embodiments provide a mobile imaging system including a body having reduced weight to support an imaging assembly of identical mass in the transport condition, because the imaging assembly is retracted in relation to the base assembly. Embodiments provide a mobile imaging system capable of supporting a heavier imaging assembly for the same reason. Embodiments provide a mobile imaging system having improved positioning flexibility around surgical tables, improved maneuverability for transporting the mobile imaging system between imaging locations within a facility, reduced requirements for materials to manufacture each system, and reduced cost of shipping systems.

CONCLUSION

An apparatus for medical imaging is described. Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. One of ordinary skill in the art will appreciate that other implementations can be made and provide the required function.

In particular, one of skill in the art will readily appreciate that the names of the apparatus are not intended to limit embodiments. Furthermore, additional apparatus can be added to the components, functions can be rearranged among the components, and new components to correspond to future enhancements and physical devices used in embodiments can be introduced without departing from the scope of embodiments. The terminology used herein with respect to medical imaging is meant to include all imaging environments and alternate technologies which provide the same functionality as described.

We claim:

1. An apparatus for imaging a subject, the apparatus comprising:
   an imaging assembly for imaging the subject;
   a base assembly including a set of wheels for rolling movement on a floor to transport the base assembly between locations and including a body the body having a recessed dock, wherein the recessed dock is adapted to receive a portion of the imaging assembly; and
   a movable support assembly connected between the base assembly and the imaging assembly for supporting the imaging assembly on the base assembly and for extending and retracting the imaging assembly from the base assembly, the movable support assembly including a lift column supported by the base, the movable support assembly including a cross arm connected between the lift column and the imaging assembly to support the imaging assembly in relation to the lift column, the lift column having a bearing block, the cross arm including a hydraulically operable telescoping arrangement of stacked tubular members, wherein the telescoping arrangement of the cross arm is moved in a forward direction to a front position relative to the bearing block.

2. The apparatus for imaging a subject according to claim 1, wherein the recessed dock being adapted to receive a capture unit of the imaging assembly.

3. The apparatus for imaging a subject according to claim 1, and the apparatus further comprising:
   the movable support assembly including a cross arm connected between the lift column and the imaging assembly to support the imaging assembly in relation to the lift column, at least one of the lift column being supported for translational movement relative to the body and a portion of the cross arm being supported for movement relative to the lift column.

4. The apparatus for imaging a subject according to claim 3, and the apparatus further comprising:
   the cross arm including a telescoping arrangement of stacked members.

5. The apparatus for imaging a subject according to claim 1, and the apparatus further comprising:
   the base assembly including a body and a stabilizing foot adapted for engagement with the floor, the stabilizing foot being movable relative to the body.

6. The apparatus for imaging a subject according to claim 1, and the apparatus further comprising:
   the imaging assembly being a C-arm imaging assembly having spaced distal ends supported by a back segment.

7. An apparatus for imaging a subject, the apparatus comprising:
   an imaging assembly for imaging the subject;
   a base assembly having a body and a front end portion adjacent the imaging assembly, the front end portion having therein a recessed dock, wherein the recessed dock being adapted to receive a portion of the imaging assembly, the base assembly having a rear end spaced in the rearward direction from the front end portion, the rear end defining a vertical rear plane extending in the vertical direction and perpendicular to the forward and rearward directions, the base assembly including a set of wheels for rolling movement on a floor, the set of wheels supporting the body in a transport condition during transport between different imaging locations in a facility; and
   a movable support assembly connected between the base assembly and the imaging assembly for supporting the imaging assembly on the base assembly and for extending and retracting the imaging assembly from the base assembly, in the transport condition the movable support assembly supporting the imaging assembly in a retracted position relative to the body, in a stationary imaging condition the movable support assembly supporting the imaging assembly in an extended position relative to the body, the apparatus having an overall length measured between the vertical rear surface and the vertical front surface, the overall length with the imaging assembly in the extended position exceeding the overall length with the imaging assembly in the retracted position, the movable support assembly including a lift column supported by the base and the lift column being moveable relative to the base, the movable support assembly including a cross arm connected between the lift column and the imaging assembly to support the imaging assembly in relation to the lift column, the lift column having a bearing block, the cross arm including a hinged arrangement of members.

8. The apparatus for imaging a subject according to claim 7, and the apparatus further comprising:
   the recessed dock being adapted to receive a capture unit of the imaging assembly when retracted.

9. The apparatus for imaging a subject according to claim 7, and the apparatus further comprising:
   the movable support assembly including a lift column supported by the base assembly, the movable support assembly including a cross arm connected between the lift column and the imaging assembly to support the imaging assembly in relation to the lift column, at least one of the lift column being supported for translational movement relative to the body and a portion of the cross arm being supported for movement relative to the lift column.

10. The apparatus for imaging a subject according to claim 9, and the apparatus further comprising:
the cross arm including a telescoping arrangement of stacked members.

11. The apparatus for imaging a subject according to claim 7, and the apparatus further comprising:
the base assembly including a body and a stabilizing foot adapted for engagement with the floor, the stabilizing foot being movable relative to the body.

12. The apparatus for imaging a subject according to claim 7, and the apparatus further comprising:
the imaging assembly being a C-arm imaging assembly having spaced distal ends supported by a back segment.

13. An apparatus for imaging a subject, the apparatus comprising:
an imaging assembly supporting an imager, the imaging assembly having an upper distal end spaced from a lower distal end, the spaced upper and lower distal ends cooperating to define a front opening facing in a forward direction, a vertical front surface having a recessed dock perpendicular to the forward direction being defined by intersecting at least one of the upper and lower distal ends, the imaging assembly having a back segment opposite and spaced from the front opening in a rearward direction opposite the forward direction, the back segment extending between and supporting the upper and lower distal ends, the recessed dock is adapted to receive a portion of the back segment of the imaging assembly;
a base assembly supporting the imaging assembly, the base assembly including a body, the body having a front end portion adjacent the back segment of the imaging assembly, the body having a rear end spaced in the rearward direction from the front end portion, the rear end defining a vertical rear surface extending in the vertical direction and perpendicular to the forward and rearward directions, the base assembly including a set of wheels for rolling movement on a floor, the set of wheels supporting the body in a transport condition during transport between different imaging locations; and
a movable support assembly connected between the base assembly and the imaging assembly for supporting the imaging assembly, the movable support assembly being selectively operable to move the imaging assembly relative to the body between an extended position and the retracted position, in the transport condition the base assembly supporting the imaging assembly in the retracted position, in the retracted position the back segment of the imaging assembly being adjacent the front end portion of the body, in the retracted position no portion of the base assembly extending in the rear direction beyond the vertical rear surface, in each imaging location the base assembly being in a stationary imaging condition, in the stationary imaging condition the base assembly supporting the imaging assembly in the extended position, in the extended position the back segment of the imaging assembly being spaced apart in the forward direction from the front end portion of the body, the apparatus having an overall length measured between the vertical rear surface and the vertical front surface, the overall length with the imaging assembly in the extended position exceeding the overall length with the imaging assembly in the retracted position.

14. The apparatus for imaging a subject according to claim 13, wherein the dock being adapted to receive a capture unit of the imaging assembly in the retracted position.

15. The apparatus for imaging a subject according to claim 13, and the apparatus further comprising:
the movable support assembly including a lift column supported by the body, the lift column extending generally in the vertical direction, the movable support assembly including a cross arm extending generally in the horizontal direction, the cross arm being connected to and supporting the imaging assembly, a portion of the cross arm being supported for movement relative to the lift column, the cross arm being selectively operable to move in the forward direction bringing the imaging assembly into the extended position and the cross arm being selectively operable to move in the rearward direction bringing the imaging assembly into the retracted position.

16. The apparatus for imaging a subject according to claim 15, and the apparatus further comprising:
the cross arm including a telescoping arrangement of stacked members.

17. The apparatus for imaging a subject according to claim 15, wherein the lift column being moveable relative to the base.

18. The apparatus for imaging a subject according to claim 13, and the apparatus further comprising:
the movable support assembly including a lift column extending generally in the vertical direction, the lift column being supported for translational movement relative to the body in the forward and rearward directions between a forward position and a rear position, the movable support assembly including a cross arm supported by the lift column and extending generally in the horizontal direction, the cross arm being connected to and supporting the imaging assembly, the lift column in the forward position bringing the imaging assembly into the extended position, the lift column in the rear position bringing the imaging assembly into the retracted position.

19. The apparatus for imaging a subject according to claim 13, and the apparatus further comprising:
the base assembly including a stabilizing foot adapted for engagement with the floor, the stabilizing foot being movable relative to the body in the forward and rearward directions, in a transport position the stabilizing foot being retracted in the rearward direction relative to the body, in a stationary support position the stabilizing foot being extended in the forward direction relative to the body.

20. The apparatus for imaging a subject according to claim 13, and the apparatus further comprising:
the imaging assembly being a C-arm imaging assembly having spaced distal ends supported by a back segment.

* * * * *